(12) United States Patent
Tout et al.

(10) Patent No.: US 8,771,240 B2
(45) Date of Patent: Jul. 8, 2014

(54) APPARATUSES, SYSTEMS, AND METHODS FOR MANAGING LIQUID FLOW ASSOCIATED WITH A TISSUE SITE USING THE PRESENCE OF REDUCED PRESSURE

(71) Applicant: KCI Licensing, Inc., San Antonio, TX (US)

(72) Inventors: Aidan Marcus Tout, Alderbury (GB); Christopher Brian Locke, Bournemouth (GB)

(73) Assignee: KCI Licensing, Inc., San Antonio, TX (US)

( * ) Notice: Subject to any disclaimer, the term of this patent is extended or adjusted under 35 U.S.C. 154(b) by 0 days.

(21) Appl. No.: 13/931,089

(22) Filed: Jun. 28, 2013

(65) Prior Publication Data
US 2013/0289503 A1    Oct. 31, 2013

Related U.S. Application Data

(62) Division of application No. 12/640,511, filed on Dec. 17, 2009, now Pat. No. 8,491,540.

(60) Provisional application No. 61/141,609, filed on Dec. 30, 2008.

(51) Int. Cl.
*A61M 5/00*  (2006.01)

(52) U.S. Cl.
USPC ........... 604/246; 604/118; 604/119; 604/120; 604/243; 604/247; 604/248; 604/249; 604/250

(58) Field of Classification Search
USPC .......................... 604/243, 118–120, 246–250
See application file for complete search history.

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 A1 | 3/1986 |
| AU | 745271 | 4/1999 |

(Continued)

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (certified translation).

(Continued)

*Primary Examiner* — Kevin C Sirmons
*Assistant Examiner* — Edelmira Bosques

(57) ABSTRACT

The illustrative embodiments described herein are directed to apparatuses, systems, and methods for managing liquid flow associated with a tissue site that involves using reduced pressure to control fluid flow. In one instance, an apparatus includes a first valve and a second valve in fluid communication with a reduced-pressure source. The valves are movable between an open position and a closed position and are operable to change flow status (open to closed or vice versa) based on a presence of reduced pressure. At least one of the first valve or the second valve is in the closed position to obstruct a flow of a liquid while the other is in the open position. The apparatus also includes a reservoir fluidly coupled to the first valve and the second valve. Other systems, methods, and apparatuses are presented.

18 Claims, 4 Drawing Sheets

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielson |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,935,005 A * | 6/1990 | Haines .............................. 604/30 |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2008/0200905 A1 | 8/2008 | Heaton et al. |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| SG | 71559 | 4/2002 |
| WO | 80/02182 | 10/1980 |
| WO | 87/04626 | 8/1987 |
| WO | 90/10424 | 9/1990 |
| WO | 93/09727 | 5/1993 |
| WO | 94/20041 | 9/1994 |
| WO | 95/03078 | 2/1995 |
| WO | 96/05873 | 2/1996 |
| WO | 97/18007 | 5/1997 |
| WO | 99/13793 | 3/1999 |

OTHER PUBLICATIONS

Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.

(56) References Cited

OTHER PUBLICATIONS

S.E. Greer, et al "The Use of Subatmospheric Pressure Dressing Therapy to Close Lymphocutaneous Fistulas of the Groin" British Journal of Plastic Surgery (2000), vol. 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, p. 1.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., vol. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinović, V. Đukić, Ž. Maksimović, Đ. Radak, and P. Peška, "Vacuum Therapy in the Treatment of Peripheral Blood Vessels," Timok Medical Journal 11 (1986), pp. 161-164 (certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, "An Improved Sump Drain-Irrigation Device of Simple Construction," Archives of Surgery 105 (1972) pp. 511-513.

C.E. Tennant, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians (Jul. 2007).

\* cited by examiner

APPARATUSES, SYSTEMS, AND METHODS FOR MANAGING LIQUID FLOW ASSOCIATED WITH A TISSUE SITE USING THE PRESENCE OF REDUCED PRESSURE

RELATED APPLICATION

This application is a Divisional of U.S. patent application Ser. No. 12/640,511, filed Dec. 17, 2009, which claims the benefit, under 35 U.S.C §119(e), of the filing of U.S. Provisional Patent Application Ser. No. 61/141,609 entitled "Apparatuses, Systems, and Methods for Managing Liquid flow Associated with a Tissue Site Based on the Presence of Reduced Pressure," filed Dec. 30, 2008, both of which are incorporated herein by reference for all purposes.

BACKGROUND

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, including faster healing, and increased formulation of granulation tissue.

SUMMARY

To alleviate existing problems with medical treatment systems, the illustrative embodiments described herein are directed to apparatuses, systems, and methods for managing liquid flow associated with a tissue site. According to an illustrative, non-limiting embodiment, a system for managing liquid flow associated with a tissue site includes a liquid source operable to supply liquid, a reduced-pressure source operable to supply reduced pressure, and a first valve in fluid communication with the reduced-pressure source. The first valve is movable between an open position and a closed position and is operable to be activated based on a presence of reduced pressure. The system further includes a second valve in fluid communication with the reduced-pressure source. The second valve is also movable between an open position and a closed position and is operable to be activated based on the presence of reduced pressure. At least one of the first valve and the second valve is in the closed position to obstruct a flow of a liquid when under reduced pressure. The system further includes a reservoir fluidly coupled to the first valve and the second valve. The reservoir is operable to contain liquid from the liquid source. The system further includes a first delivery conduit that is in fluid communication with the reservoir and is operable to deliver the liquid from the liquid source. The system also includes a second delivery conduit that is in fluid communication with the reservoir and is operable to deliver the liquid from the reservoir to the tissue site.

According to another illustrative, non-limiting embodiment, an apparatus for managing liquid flow associated with a tissue site includes a first valve in fluid communication with a reduced-pressure source. The first valve is movable between an open position and a closed position and is operable to be activated based on a presence of reduced pressure. The apparatus further includes a second valve in fluid communication with the reduced-pressure source. The second valve is movable between an open position and a closed position and is operable to be activated based on the presence of reduced pressure. At least one of the first valve and the second valve is in the closed position to obstruct a flow of liquid when experiencing reduced pressure. The apparatus also includes a reservoir fluidly coupled to the first valve and the second valve. The reservoir is operable to receive liquid from a liquid source when the first valve is in the open position.

According to another illustrative, non-limiting embodiment, a method for managing liquid flow associated with a tissue site includes providing a valve arrangement having a first valve, a second valve, and a reservoir, and receiving reduced pressure at the first valve and the second valve. The first valve and second valve each have an open position and a closed position. The method further includes changing a flow status (open to closed or vice versa) of the first valve in response to receiving reduced pressure at the first valve, receiving a liquid at the reservoir when the first valve is open, changing a flow status of the second valve in response to receiving reduced pressure at the second valve, and obstructing a flow of liquid from the reservoir when the second valve is closed.

According to another illustrative, non-limiting embodiment, a method for managing liquid flow associated with a tissue site includes providing a valve arrangement with a first valve, a second valve, and a reservoir. The method also includes fluidly coupling the first valve to a liquid source, fluidly coupling the second valve to the tissue site, changing a position of the first valve to one of an open position and a closed position based on a presence of reduced pressure at the first valve, and changing a position of the second valve to the other of the open position and the closed position based on a presence of reduced pressure at the second valve.

According to another illustrative, non-limiting embodiment, a method of manufacturing an apparatus for managing liquid flow associated with a tissue site includes providing a first valve moveable between an open position and a closed position and operable to change flow status based on a presence of reduced pressure, providing a second valve moveable between an open position and a closed position and operable to change flow status based on the presence of reduced pressure, and providing a reservoir operable to contain a liquid. The method further includes coupling the reservoir to the first valve and the second valve such that the reservoir is disposed between the first valve and the second valve.

According to another illustrative, non-limiting embodiment, a method of manufacturing an apparatus for managing liquid flow associated with a tissue site includes providing a first sheet, providing a second sheet, providing a foam member, and coupling the first sheet to the second sheet to form a reduced-pressure conduit, a reservoir, a first valve, and a second valve. The foam member is enclosed between the first sheet and the second sheet.

Other features and advantages of the illustrative, non-limiting embodiments will become apparent with reference to the drawings and detailed description that follow.

BRIEF DESCRIPTION OF THE DRAWINGS

A more complete understanding may be obtained by reference to the following Detailed Description when taken in conjunction with the accompanying Drawings, wherein like numerals indicate like elements throughout, and wherein.

DETAILED DESCRIPTION OF ILLUSTRATIVE EMBODIMENTS

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

Figure 1:
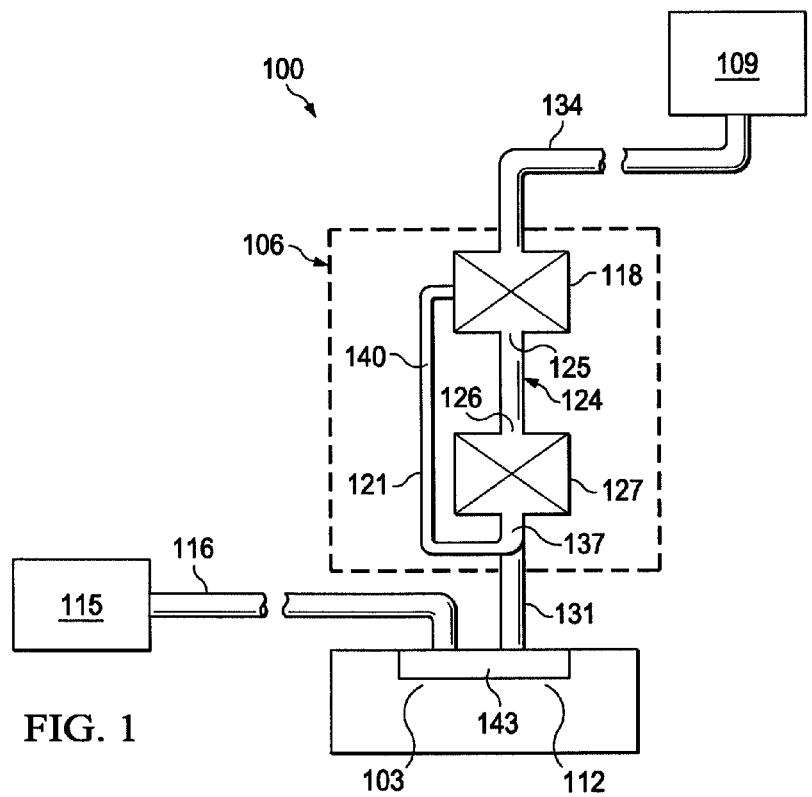
FIG. 1 is a schematic diagram of a treatment system for managing liquid flow associated with a tissue site in accordance with an illustrative embodiment.

Referring primarily to FIG. 1, a system 100 for managing liquid flow associated with a tissue site 103 is shown according to an illustrative embodiment. An apparatus 106, or valve arrangement, which is included in the system 100, manages the flow of liquid from a liquid source 109 to the tissue site 103. The apparatus 106 may control, the amount of liquid that flows to the tissue site 103, including whether the liquid flows to the tissue site 103 at all. The apparatus 106 uses reduced pressure from a reduced-pressure source 115 to help manage liquid flow from the liquid source 109 to the tissue site 103.

As used herein, "reduced pressure" generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure at the tissue site. Unless otherwise indicated, values of pressure stated herein are gauge pressures. The reduced pressure delivered may be constant or varied (patterned or random) and may be delivered continuously or intermittently. Although the terms "vacuum" and "negative pressure" may be used to describe the pressure applied to the tissue site, the actual pressure applied to the tissue site may be more than the pressure normally associated with a complete vacuum. Consistent with the use herein, an increase in reduced pressure or vacuum pressure typically refers to a relative reduction in absolute pressure. Unless otherwise indicated, as used herein, "or" does not require mutual exclusivity.

The reduced-pressure source 115 supplies reduced pressure to the apparatus 106 via the tissue site 103. The reduced pressure may be supplied from the reduced-pressure source 115 to the tissue site 103 through a conduit 116. Residual reduced pressure may continue to be supplied by at least a portion 112 of the tissue site 103 to the apparatus 106 even when the reduced-pressure source 115 is turned off—at least until the reduced pressure in the tissue site is disseminated. The reduced-pressure source 115 may be any device or system that generates or provides a reduced pressure, including, but not limited to, manually operated or powered pumps or wall suction. As non-limiting examples, the reduced-pressure source 115 may include devices that are manually actuated, battery operated, or any form of pneumatic pump. In one example, the pump uses low amounts of power and is capable of operating for an extended period of time on a single charge of the battery. As another non-limiting example, the reduced-pressure source 115 may be wall suction. As shown by the non-limiting examples, the possibilities for the reduced-pressure source 115 are numerous.

The liquid source 109 supplies liquid to the tissue site 103 via the apparatus 106. The liquid source 109 may be any container, bag, or other device capable of holding a liquid. The liquid supplied by the liquid source 109 may be any liquid, including liquids that contain solid particles. In one example, the liquid supplied by the liquid source 109 may facilitate the healing or growth of the tissue site 103. The liquid supplied by the liquid source 109 may contain growth factors, healing factors, antibiotics, medicines, etc.

The tissue site 103 may be the bodily tissue of any human, animal, or other organism, including adipose tissue, muscle tissue, dermal tissue, vascular tissue, connective tissue, cartilage, tendons, ligaments, bone, or any other tissue. While the tissue site 103 may include a wound (including an open wound or an incision), diseased tissue, or defective tissue, the tissue site 103 may also be healthy tissue that is not wounded, diseased, or defective. The application of reduced pressure to the tissue site 103 may be used to promote the drainage of exudate and other liquids from the tissue site 103, as well as stimulate the growth of additional tissue. In the case in which the tissue site 103 is a wound site, the growth of granulation tissue and removal of exudates and bacteria promotes healing of the wound. The application of reduced pressure to non-wounded or non-defective tissue, including healthy tissue, may be used to promote the growth of tissue that may be harvested and transplanted to another tissue location. The delivery of liquid from the liquid source 109 to the tissue site 103 via the apparatus 106 may be used in conjunction with the application of reduced pressure to the tissue site 103 to facilitate the healing, growth, or other treatment of the tissue site 103.

The apparatus 106 for managing liquid flow to the tissue site 103 includes a first valve 118 in fluid communication with the reduced-pressure source 115. In one example, fluid communication between the first valve 118 and the reduced-pressure source 115 may be provided, at least in part, by an intermediate reduced-pressure conduit, or reduced-pressure conduit 121. The first valve 118 is movable between an open position and a closed position. In an open position, the first valve 118 may be partially or fully open, and liquid from the liquid source 109 is allowed to pass through the first valve 118 and into a reservoir 124 that is operable to contain the liquid. In a closed position, the first valve 118 may be partially or fully closed, and the first valve 118 obstructs or prevents the flow of liquid from the liquid source 109 into the reservoir 124.

The first valve 118 is activated, or changes flow status, i.e., moves from the open position to the closed position or vice versa, based on a presence or absence of reduced pressure at the first valve 118. The reduced pressure may be transferred to the first valve 118 from the reduced-pressure source 115 to the first valve 118 at least in part by the reduced-pressure conduit 121. In one example, the first valve 118 moves from a closed position to an open position in the presence of reduced pressure at the first valve 118, and the first valve 118 moves from an open position to a closed position in an absence of reduced pressure at the first valve 118. As used herein, an "absence" of reduced pressure may include a partial or total absence of reduced pressure.

The apparatus 106 also includes a second valve 127 in fluid communication with the reduced-pressure source 115. In one example, fluid communication between the second valve 127 and the reduced-pressure source 115 may be at least partially provided by the reduced-pressure conduit 121. In the example in which the reduced-pressure conduit 121 provides fluid communication between the second valve 127 and the reduced-pressure source 115, the reduced-pressure conduit 121 may be an air-permeable material, a portion of which extends into a second delivery conduit 131. The second valve 127 is activated, or changes flow status, i.e., moves from an open position to a closed position or vice versa, based on the presence or absence of reduced pressure. In an open position, the second valve 127 may be partially or fully open, and liquid from the reservoir 124 is allowed to pass through the second valve 127, into the second delivery conduit 131, and to the tissue site 103. In the closed position, the second valve 127 may be partially or fully closed, and the second valve 127 obstructs or prevents the flow of liquid to the into the second delivery conduit 131 and thus to the tissue site 103.

In one example, the second valve 127 moves between the open position or the closed position based on a presence of reduced pressure at the second valve 127. In this example, the reduced pressure may be transferred to the second valve 127 from the reduced-pressure source 115, at least in part, by the reduced-pressure conduit 121 and the second delivery conduit 131. In one example, the second valve 127 moves from an open position to a closed position in the presence of reduced pressure at the second valve 127, and the second valve 127 moves from a closed position to an open position in an absence of reduced pressure at the second valve 127.

Numerous valve types may be used for the first valve 118 and the second valve 127. In one embodiment, the first valve 118 and the second valve 127 are pilot-actuated valves. In one example of this embodiment, the first valve 118 and the second valve 127 may include a master and slave cylinder, and may be made from machined brass. In another embodiment, the first valve 118 and the second valve 127 may be diaphragm valves.

In one embodiment, the reservoir 124 is operable to contain a liquid and transport the liquid from the first valve 118 to the second valve 127. The reservoir 124 may be disposed between the first valve 118 and the second valve 127. In one non-limiting example, a first end 125 of the reservoir 124 is coupled to the first valve 118, and a second end 126, which is opposite the first end 125, of the reservoir 124 is coupled to the second valve 127. As used herein, the term "coupled" includes coupling via a separate object, and also includes direct coupling. In the case of direct coupling, the two coupled objects touch each other in some way. The term "coupled" also encompasses two or more components that are continuous with one another by virtue of each of the components being formed from the same piece of material. Also, the term "coupled" includes chemical coupling, such as via a chemical bond. The term "coupled" may also include mechanical, thermal, or electrical coupling. The term "coupled" may also include fluidly coupled, in which case a first object that is coupled to a second object is in fluid communication with that second object.

As shown in the illustrative embodiments disclosed herein, the volumetric capacity of the reservoir 124 may be varied. For example, the size of the reservoir 124 may be increased or decreased to vary the volumetric capacity of the reservoir 124. In one non-limiting example, the reservoir 124 may have a volumetric capacity that corresponds to a predetermined medicinal dosage such that the predetermine dosage of medicinal liquid is delivered to the tissue site 103 when the second valve 127 moves to an open position.

In one illustrative embodiment, the reservoir 124 may be flexible, in which case the volume of the reservoir 124 may vary depending on the amount of liquid in the reservoir 124. The flexibility of the reservoir 124 may facilitate the movement of liquid out of the reservoir 124. In another illustrative embodiment, the reservoir 124 may be a rigid container. The reservoir 124 may also include a vent line (not shown) that permits the entry of a gas, such as air, into the reservoir 124. The vent line may facilitate the movement of liquid out of the reservoir 124 and toward the tissue site 103. The vent line may be associated with the liquid source 109 or a first delivery conduit 134. Additional illustrative, non-limiting embodiments suitable for use as the reservoir 124 are provided below in FIGS. 2-5.

In one illustrative, non-limiting embodiment, the valves 118, 127 are configured to operate according to the following TABLE 1.

TABLE 1

| Pressure Status At Tissue Site | First Valve 118 | Second Valve 127 |
| --- | --- | --- |
| Reduced Pressure Present | Open | Closed |
| Reduced Pressure Not Present | Closed | Open |

The position of the valves could be readily changed to be the opposite of what is shown in TABLE 1 for the different pressure statuses as shown in TABLE 2.

TABLE 2

| Pressure Status At Tissue Site | First Valve 118 | Second Valve 127 |
| --- | --- | --- |
| Reduced Pressure Present | Closed | Open |
| Reduced Pressure Not Present | Open | Closed |

At least one of the first valve 118 and the second valve 127 is in a closed position to obstruct or prevent the flow of the liquid. In the illustrative, non-limiting example represented in TABLE 1, the first valve 118 has one of an open position or a closed position and the second valve 127 has the other of the open position or the closed position such that the first valve 118 and the second valve 127 each have different positions. When reduced pressure is present at the tissue site 103, the reduced pressure may be transferred to the first valve 118 and the second valve 127 by conduits 131 and 121 to cause the first valve 118 to have an open position and the second valve 127 to have a closed position. When the first valve 118 is in an open position and the second valve 127 is in a closed position, liquid is allowed to move from the liquid source 109 to the reservoir 124, but the second valve 127 obstructs or prevents the liquid from moving into conduits 121 and 131 and thus to the tissue site 103. The reservoir 124 may then be allowed to fill to a predetermined volume, such as a predetermined medicinal dosage.

The absence of reduced pressure at the tissue site 103 may cause the first valve 118 to have a closed position and the second valve 127 to have an open position. When the first valve 118 has a closed position and the second valve 127 has an open position, liquid is allowed to move from the reservoir 124 to the tissue site 103, but the first valve 118 obstructs or prevents the liquid from moving to the reservoir 124 from the liquid source 109. Thus, the predetermined volume of liquid in the reservoir 124 is delivered to the tissue site 103 while the first valve 118 helps to prevent additional liquid from being added to the predetermined volume of liquid delivered from the reservoir 124.

In one embodiment, the system 100 includes the first delivery conduit 134 that is in fluid communication with the first valve 118, and when the first valve 118 is open, with reservoir 124. The first delivery conduit 134 is operable to deliver the liquid from the liquid source 109 to the apparatus 106. The first delivery conduit 134 may deliver liquid from the liquid source 109 to the reservoir 124 when the first valve 118 is in an open position.

In one embodiment, the system 100 includes the second delivery conduit 131 that is in fluid communication with the reservoir 124 when the second valve 127 is in the open position. The second delivery conduit 131 is operable to deliver liquid from the apparatus 106 to the tissue site 103. For example, liquid may be delivered from the reservoir 124 to the tissue site 103 via the second delivery conduit 131. In this example, the second delivery conduit 131 may deliver liquid from the reservoir 124 to the tissue site 103 when the second valve 127 is in the open position.

In one illustrative embodiment, the reduced-pressure conduit 121 fluidly couples the first valve 118 and the second delivery conduit 131. In addition, the reduced-pressure conduit 121 may fluidly couple the first valve 118 and the second valve 127. In the illustrative embodiment of FIG. 1, reduced pressure is delivered through the second delivery conduit 131 to the reduced-pressure conduit 121, which delivers the reduced pressure to the first valve 118 and the second valve 127.

In one non-limiting example, reduced pressure from the tissue site 103 is transferred to the reduced-pressure conduit 121 by the second delivery conduit 131. The reduced-pressure conduit 121 has a first portion 140 and a second portion 137. The first portion 140 of the reduced-pressure conduit 121 transfers reduced pressure from the second delivery conduit 131 to the first valve 118. The second portion 137 of the reduced-pressure conduit 121 transfers reduced pressure from the second delivery conduit 131 to the second valve 127.

In another non-limiting example, the second delivery conduit 131 may directly deliver reduced pressure from the tissue site 103 to the second valve 127 without the intervening reduced-pressure conduit 121 (or alternatively, the second portion 137 may comprise a portion of the second delivery conduit 131). In this non-limiting example, the reduced-pressure conduit 121 may be in fluid communication with the first valve 118, and may be operable to transmit reduced pressure directly from the tissue site 103 to the first valve 118. Also, in this non-limiting example, the reduced-pressure conduit 121 may be fluidly coupled to the second delivery conduit 131 or the tissue site 103.

The system 100 may also include a manifold 143 that may be placed adjacent or in contact with the tissue site 103. The manifold 143 may distribute the liquid received from the apparatus 106 to the tissue site 103. The manifold 143 may be a biocompatible, porous material that is capable of being placed in contact with the tissue site 103 and distributing reduced pressure or liquid to the tissue site 103. The manifold 143 may be made from foam, gauze, felted mat, or other suitable material or structure that distributes reduced pressure. The manifold 143 may include a plurality of flow channels or pathways to facilitate distribution of reduced pressure or liquid to or from tissue site 101.

The manifold 143 may further serve as a scaffold for new cell-growth, or a scaffold material may be used in conjunction with the manifold 143 to promote cell-growth. A scaffold is a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials. In one example, the scaffold material has a high void-fraction (i.e. a high content of air). In another embodiment, the system 100 does not include the manifold 143.

By using reduced pressure from the reduced-pressure source 115, the system 100 is able to effectively manage the flow of liquid from the liquid source 109 to the tissue site 103. Measured dosages of liquid, such as a medicinal liquid, may be released from the reservoir 124 to the tissue site 103 at predetermined time intervals. For example, reduced pressure from the reduced-pressure source 115 may be applied to the tissue site 103 in a cyclic manner to determine when liquid is released from the reservoir 124 to the tissue site 103. In this example, when the reduced-pressure source 115 applies reduced pressure to the tissue site 103, the reduced pressure is transferred to the first valve 118 and the second valve 127 to cause the first valve 118 to have an open position and the second valve 127 to have a closed position. Thus, liquid is allowed to flow from the liquid source 109 to the reservoir 124, but is obstructed from flowing from the reservoir 124 to the tissue site 103. When the reduced-pressure source 115 ceases to apply reduced pressure to the tissue site 103, thereby causing an absence of reduced pressure at the tissue site 103, the first valve 118 may transition to a closed position and the second valve 127 transition to an open position. Thus, a measured dosage of liquid in the reservoir 124 is allowed to flow to the tissue site 103, and the first valve 118 obstructs liquid from flowing into the reservoir 124 from the liquid source 109. In this manner, the reduced pressure applied to the tissue site 103 by the reduced-pressure source 115 may be cycled to manage the application of liquid to the tissue site 103.

In one embodiment, a method for managing liquid flow associated with the tissue site 103 may include receiving reduced pressure at the first valve 118 and the second valve 127. The reduced pressure may be received by the first valve 118 and the second valve 127 via the reduced-pressure conduit 121 or the second delivery conduit 131. The method may also include opening the first valve 118 in response to receiving reduced pressure at the first valve 118. The method may also include receiving a liquid at the reservoir 124 in response to opening the first valve 118. The method may also include closing the second valve 127 in response to receiving reduced pressure at the second valve 127. The method may also include obstructing a flow of liquid from the reservoir 124 in response to closing the second valve 127. "Obstructing" includes partially or fully obstructing.

In one embodiment, the method may also include closing the first valve 118 in response to an absence of reduced pressure at the first valve 118. The reduced-pressure source 115 may cease to supply reduced pressure to the tissue site 103 and thus cause an absence of reduced pressure at the first valve 118. The method may also include obstructing the flow of liquid from the liquid source 109 to the reservoir 124 in response to closing the first valve 118. The second valve 127 may open in response to the absence of reduced pressure at the second valve 127. The tissue site 103 may then receive liquid from the reservoir 124 in response to opening the second valve 127.

In another embodiment, a method for managing liquid flow associated with the tissue site 103 may include changing a position of the first valve 118 to one of an open position or a closed position based on the presence of reduced pressure at the first valve 118. The method also includes changing a position of the second valve 127 to the other of the open position or the closed position. The method may also include obstructing a flow of liquid using the valve having the closed position, which, in this embodiment, may be either the first valve 118 or the second valve 127.

In one example, changing the position of the first valve 118 to one of the open position or the closed position based on the presence of reduced pressure at the first valve 118 includes changing the position of the first valve 118 from the closed position to the open position in the presence of reduced pressure. In another example, changing the position of the first valve 118 to one of the open position or the closed position based on the presence of reduced pressure at the first valve 118 includes changing the position of the first valve 118 from the open position to the closed position in an absence of reduced pressure. In another example, the first valve 118 is in the closed position, and obstructing the flow of liquid using the valve having the closed position includes obstructing the liquid from being received by the reservoir 124 using the first valve 118. In another example, the method may include receiving liquid at the reservoir 124 when the first valve 118 is in the open position.

In one example, changing the position of the second valve 127 to the other of the open position or the closed position includes changing the position of the second valve 127 from the open position to the closed position in the presence of reduced pressure. In another example, the second valve 127 is in the closed position, and obstructing the flow of liquid using the valve having the closed position includes obstructing the liquid from leaving the reservoir 124 using the second valve 127. In another example, changing the position of the second valve 127 to the other of the open position or the closed position includes changing the position of the second valve 127 from the closed position to the open position in an absence of reduced pressure. In another example, the method may include receiving liquid at the tissue site 103 when the second valve 127 is in the open position.

In one embodiment, a method of manufacturing an apparatus for managing liquid flow associated with the tissue site 103 includes providing the first valve 118, which is capable of having an open position and a closed position based on a presence of reduced pressure. The method also includes providing the second valve 127, which is capable of having an open position or a closed position based on the presence of reduced pressure. The method may also include providing the reservoir 124, which is operable to contain a liquid, and fluidly coupling the reservoir 124 to the first valve 118 and the second valve 127. The reservoir 124 may be disposed between the first valve 118 and the second valve 127.

In one example, the method of manufacturing also includes providing the reduced-pressure conduit 121, and coupling the reduced-pressure conduit 121 to at least one of the first valve 118 and the second valve 127. In this example, the reduced-pressure conduit 121 is operable to transfer reduced pressure to at least one of the first valve 118 and the second valve 127.

Referring now primarily to FIGS. 2-5, an apparatus 206, or valve arrangement, is shown according to an illustrative embodiment. The apparatus 206 may be used as the apparatus 106 in the system 100 of FIG. 1. The apparatus 206 comprises a plurality of sheets, including a first sheet 246, a second sheet 249, and a third sheet 252, as well as a foam member 255. In one embodiment, the first sheet 246, the second sheet 249, the third sheet 252, and the foam member 255 may be combined (by coupling a portion, enclosing, or other techniques) with one another to form the various components of the apparatus 206, including the first valve 218, the second valve 227, the reservoir 224, and the reduced-pressure conduit 221. The first valve 218, the second valve 227, the reservoir 224, and the reduced-pressure conduit 221 are functionally analogous to the first valve 118, the second valve 127, the reservoir 124, and the reduced-pressure conduit 121 in FIG. 1, respectively.

The first sheet 246, the second sheet 249, and the third sheet 252 may be composed of any liquid impermeable material. Non-limiting examples of the material from which the first sheet 246, the second sheet 249, and the third sheet 252 may be formed include polyvinyl chloride (PVC), polyurethane (PU), polyolefins, polyethylene (PE), polypropylene (PP), etc. In one example, the first sheet 246, the second sheet 249, and the third sheet 252 may formed from a flexible or rigid material. Although each of the first sheet 246, the second sheet 249, and the third sheet 252 may be composed of the same material, each of the first sheet 246, the second sheet 249, and the third sheet 252 may also be composed of different materials. For example, the third sheet 252 may be composed of a different material than the first sheet 246 and the second sheet 249. In one non-limiting example, the first sheet 246 and the second sheet 249 are approximately the same size and shape. Also, the third sheet 252 may be smaller than the first sheet 246 or the second sheet 249.

The first sheet 246, the second sheet 249, the third sheet 252, and the foam member 255 may be coupled to one another in a wide variety of ways to form the various components of the apparatus 206. In one embodiment, the first sheet 246 may be coupled to at least one of the second sheet 249 and the third sheet 252 along lines 258 to form the first valve 218, the second valve 227, the reservoir 224, and the reduced-pressure conduit 221. In addition to the pattern shown in FIG. 3, the lines 258 may form any pattern that provides desirable characteristics for the apparatus 206, including the various components thereof. In addition, the first sheet 246 may be coupled to at least one of the second sheet 249 and the third sheet 252 at the lines 258 in any manner, including welding (e.g., ultrasonic or RF), bonding, adhesives (e.g., silicone adhesive), cements, etc.

In one example, the first sheet 246 may be coupled to at least one of the second sheet 249 and the third sheet 252 to form the reservoir 224 and the reduced-pressure conduit 221. In this example, the first sheet 246 may be coupled to the second sheet 249 and the third sheet 252 along a portion 261 of the lines 258 to form the reservoir 224. Thus, the reservoir 224 may be at least partially formed by abutting portions of the first sheet 246 and the second sheet 249 and abutting portions of the first sheet 246 and the third sheet 252. "Abutting" may mean next to each other or near and yet spaced. In addition, the first sheet 246 may be coupled to the second sheet 249 and the third sheet 252 along a portion 264 of the lines 258 to form the reduced-pressure conduit 221. Thus, the reduced-pressure conduit 221 may be at least partially formed by abutting portions of the first sheet 246 and the second sheet 249 and abutting portions of the first sheet 246 and the third sheet 252.

The third sheet 252 may also be coupled to the second sheet 249 along lines 271 to form an inlet conduit 273. Thus, the inlet conduit 273 may be at least partially formed by abutting portions of the third sheet 252 and the second sheet 249. The inlet conduit 273 may transfer the liquid 250 to the reservoir 224. The inlet conduit 273 may also include an aperture or hole 275, and the liquid 250 may be transferred from the inlet conduit 273 to the reservoir 224 via the hole 275. The apparatus 206 also includes a first delivery conduit 234, which delivers the liquid 250 from a liquid source to the inlet conduit 273. The first delivery conduit 234 is insertable into the inlet conduit 273, and may be removably coupled to the inlet conduit 273 by any technique, including interference fit.

The apparatus 206 also includes the foam member 255, which may be disposed between the first sheet 246 and the second sheet 249 and at least partially enclosed therebetween. In addition or alternatively, a portion 267 of the foam member 255 may also be disposed between the first sheet 246 and the third sheet 252. The foam member 255 is operable to transfer reduced pressure, which may be from a reduced-pressure source, and the liquid 250, which may be from a liquid source. A portion 269 of the foam member 255 may be included between the portions of the first sheet 246 and the second sheet 249 that form the reduced-pressure conduit 221, as well as between the portions of the first sheet 246 and the third sheet 252 that form the reduced-pressure conduit 221. The portion 269 of the foam member 255 may thus transfer reduced pressure through the reduced-pressure conduit 221. In an alternative embodiment, a portion of the foam member 255 may also be used to help form the reservoir 224.

Although in the examples of FIGS. 2-5, the foam member 255 is composed of foam, the foam member 255 may be composed of any material that is capable of transferring reduced pressure or the liquid 250. The foam member 255 may be any manifold material. The foam member 255 may also be composed of compressible materials.

Figure 3:
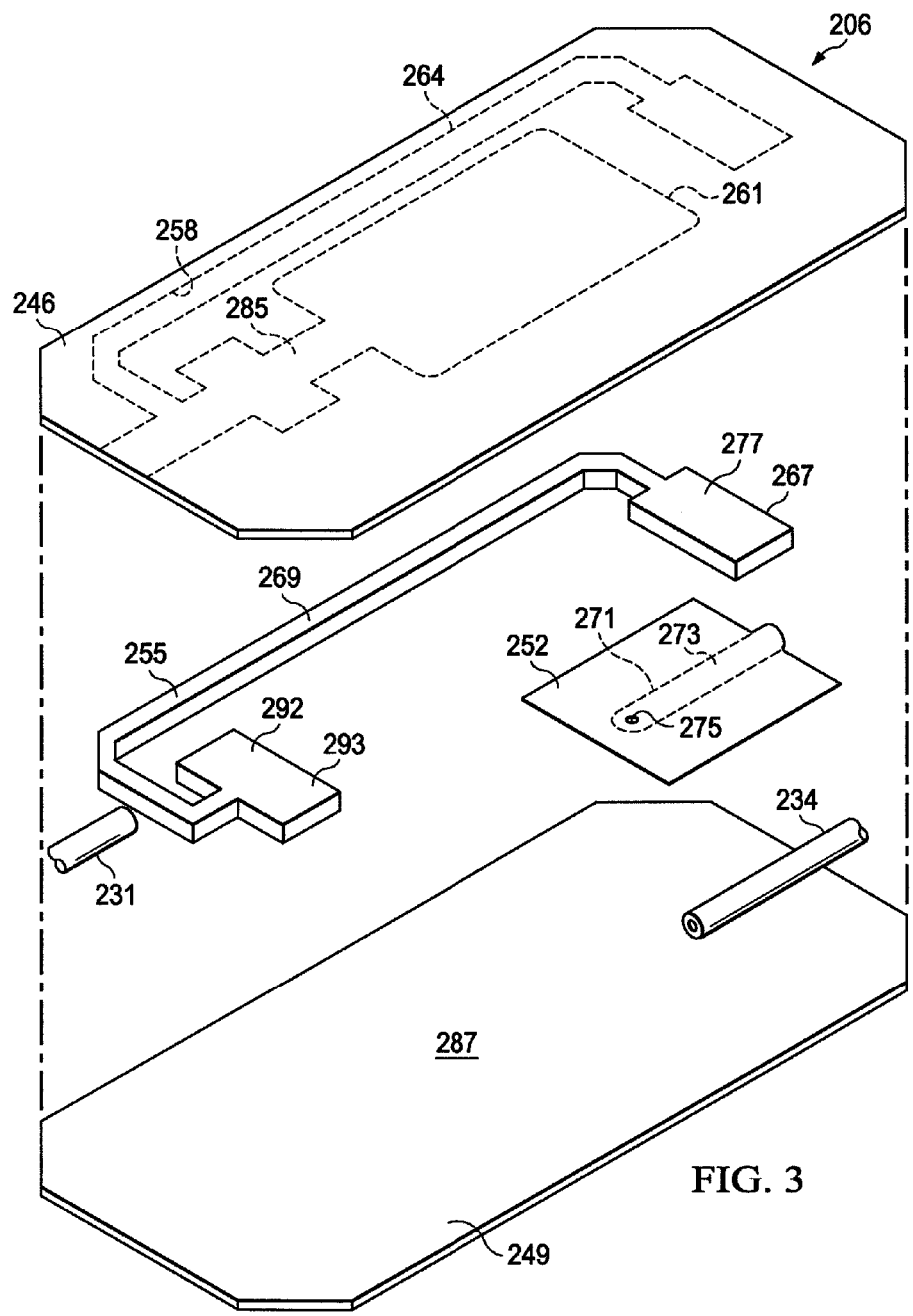
FIG. 3 is a schematic, exploded perspective view of an apparatus for managing liquid flow associated with a tissue site in accordance with an illustrative embodiment.
Figure 4:
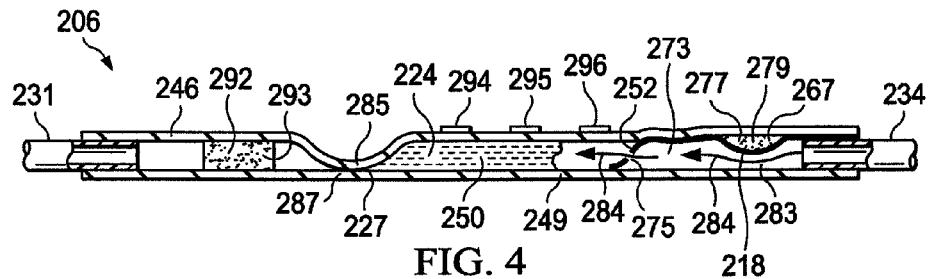
FIG. 4 is a schematic cross-sectional view of the apparatus of FIG. 2 taken along line 4-4 when at least a portion of the apparatus is exposed to reduced pressure.
Figure 5:
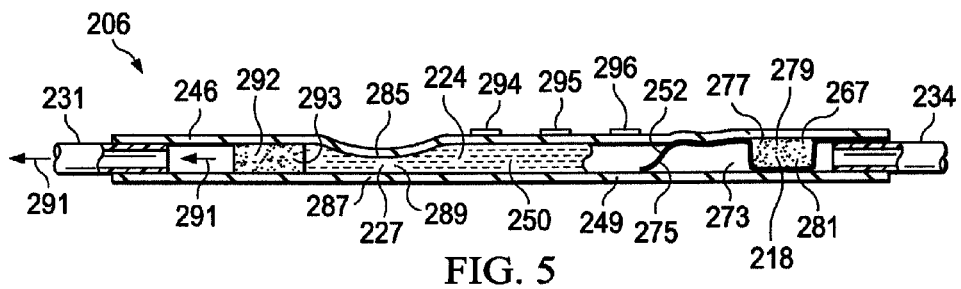
FIG. 5 is a schematic cross-sectional view of the apparatus of FIG. 2 taken along line 4-4 when reduced pressure is absent from the apparatus.

With reference primarily to FIGS. 3-5, in one embodiment, a first end 277 of the foam member 255 forms at least a portion of the first valve 218. The first end 277 of the foam member 255 may be an enlarged end portion, and may have any shape, including a rectangular, circular, diamond, elliptical, or polygonal shape. In one example, the first end 277 compresses in the presence of reduced pressure to a compressed state 279, as shown in FIG. 4. The first end 277 may expand back to an original size in an absence of reduced pressure to form an expanded state 281, as shown in FIG. 5. When the first end 277 is in the compressed state 279, the first valve 218 is in an open position. When the first end 277 is in the expanded state 281, the first valve 218 is in a closed position. Thus, when the reduced-pressure conduit 221 transfers reduced pressure to the first end 277, which forms part of the first valve 218, the first end 277 compresses to create a space 283 through which the liquid 250 may flow. In particular, the liquid 250 may flow from the first delivery conduit 234 and into the reservoir 224 via the hole 275, as indicated by arrows 284. Conversely, when reduced pressure is absent at the first end 277, the first end 277 is in the expanded state 281 to reduce or eliminate the space 283, and the liquid 250 is obstructed from flowing from the first delivery conduit 234 into the reservoir 224.

The apparatus 206 also includes the second valve 227, which may be at least partially formed by a first wall 285 and the second wall 287. The first wall 285 may be a portion of the first sheet 246, and the second wall 287 may be a portion of the second sheet 249. In one example, the first wall 285 and the second wall 287 are drawn nearer to one another in the presence of reduced pressure to form a closed position, as shown in FIG. 4. In this example, the first wall 285 and the second wall 287 may firmly abut one another to form the closed position. The first wall 285 and the second wall 287 may also move away from one another in an absence of reduced pressure to form an open position, as shown in FIG. 5. In the open position, a space 289 exists between the first wall 285 and the second wall 287 to allow the liquid 250 in the reservoir 224 to flow out of the reservoir 224 and into the second delivery conduit 231, as indicated by arrows 291. The second delivery conduit 231 may then deliver the liquid 250 to a tissue site.

When the second valve 227 is in the open position, the liquid 250 may pass through a second end 292 of the foam member 255. In addition, the movement of the first wall 285 away from the second wall 287 in the absence of reduced pressure may be assisted by the second end 292 of the foam member 255. The second end 292 of the foam member 255 may be an enlarged end portion 293. The second end 292 of the foam member 255 may bias the first wall 285 away from the second wall 287. Thus, the second end 292 of the foam member 255 assists in opening the second valve 227 in the absence of reduced pressure at the second valve 227.

The apparatus 206 may also include a set of restriction strips, e.g., 294, 295, and 296. The set of restriction strips may include one or more restriction strips. The set of restriction strips 294, 295, and 296 are disposed over at least a portion of the reservoir 224. The set of restriction strips 294, 295, and 296 are operable to restrict expansion of the reservoir 224 to contain a maximum amount of the liquid 250. Each of the set of restriction strips 294, 295, and 296 is removable from the reservoir 224 to increase the maximum amount of the liquid 250 that may be held by the reservoir 224. To provide one non-limiting example, the reservoir 224 may be able to hold 10 milliliters of the liquid 250 when restriction strips 294, 295, and 296 are applied to the reservoir 224. Restriction strip 294 may be removed from the reservoir 224 to increase the maximum amount of the liquid 250 that is holdable by the reservoir 224 to 15 milliliters. Restriction strip 295 may be removed from the reservoir 224 to increase the maximum amount of the liquid 250 that is holdable by the reservoir 224 to 20 milliliters. In addition, all of the restriction strips 294, 295, and 296 may be removed from the reservoir 224, in which case the reservoir 224 may be allowed to expand to a maximum capacity. While specific illustrative examples are provided, i.e., 10 milliliters, 15 milliliters, and 20 milliliters, it should be understood that any volume may be used for the reservoir 224 and the volume provided with restriction strips 294, 295, 296.

In another embodiment, the apparatus 206 may include a column (not shown) that is slidably coupled to the reservoir 224. The column may be slidable into a plurality of positions, and may be slidable along the length, width, or thickness of the reservoir 224. The position of the column determines a maximum amount of the liquid 250 that may be held by the reservoir 224. In one example of this embodiment, the reservoir 224 may be a syringe that has a valve on each end. The syringe may also include an internal slidable column.

In operation according to one embodiment, reduced pressure may be applied to the apparatus 206 to change the positions of the first valve 218 and the second valve 227, and thereby manage the flow of the liquid 250 to a tissue site. In FIG. 4, reduced pressure is transmitted from a reduced-pressure source, such as the reduced-pressure source 115 in FIG. 1, to the first valve 218 and the second valve 227 via the reduced-pressure conduit 221. The reduced pressure may be transmitted from the reduced-pressure source 115 via a tissue site. As shown in FIG. 4, the first valve 218 has an open position in the presence of reduced pressure at the first valve 218, and the second valve 227 has a closed position in the presence of reduced pressure at the second valve 227. Thus, in FIG. 4, the reservoir 224 receives the liquid 250 from a liquid source, and the second valve 227 obstructs the liquid 250 from flowing out of the reservoir 224. The set of restriction strips 294, 295, and 296 may restrain the expansion of the reservoir 224 such that the reservoir 224 is able to hold a predetermined maximum amount of the liquid 250. In one example, this predetermined maximum amount may be a prescribed dosage.

In FIG. 5, little or no reduced pressure is transferred from a reduced-pressure source to the first valve 218 and the second valve 227 via the reduced-pressure conduit 221. As result, as shown in FIG. 5, the first valve 218 has a closed position to obstruct the flow of the liquid 250 into the reservoir 224, and the second valve 227 has an open position to allow the liquid 250 to flow from the reservoir 224 to a tissue site. The valves 218 and 227 could be structured to open and close opposite to that described.

Figure 2:
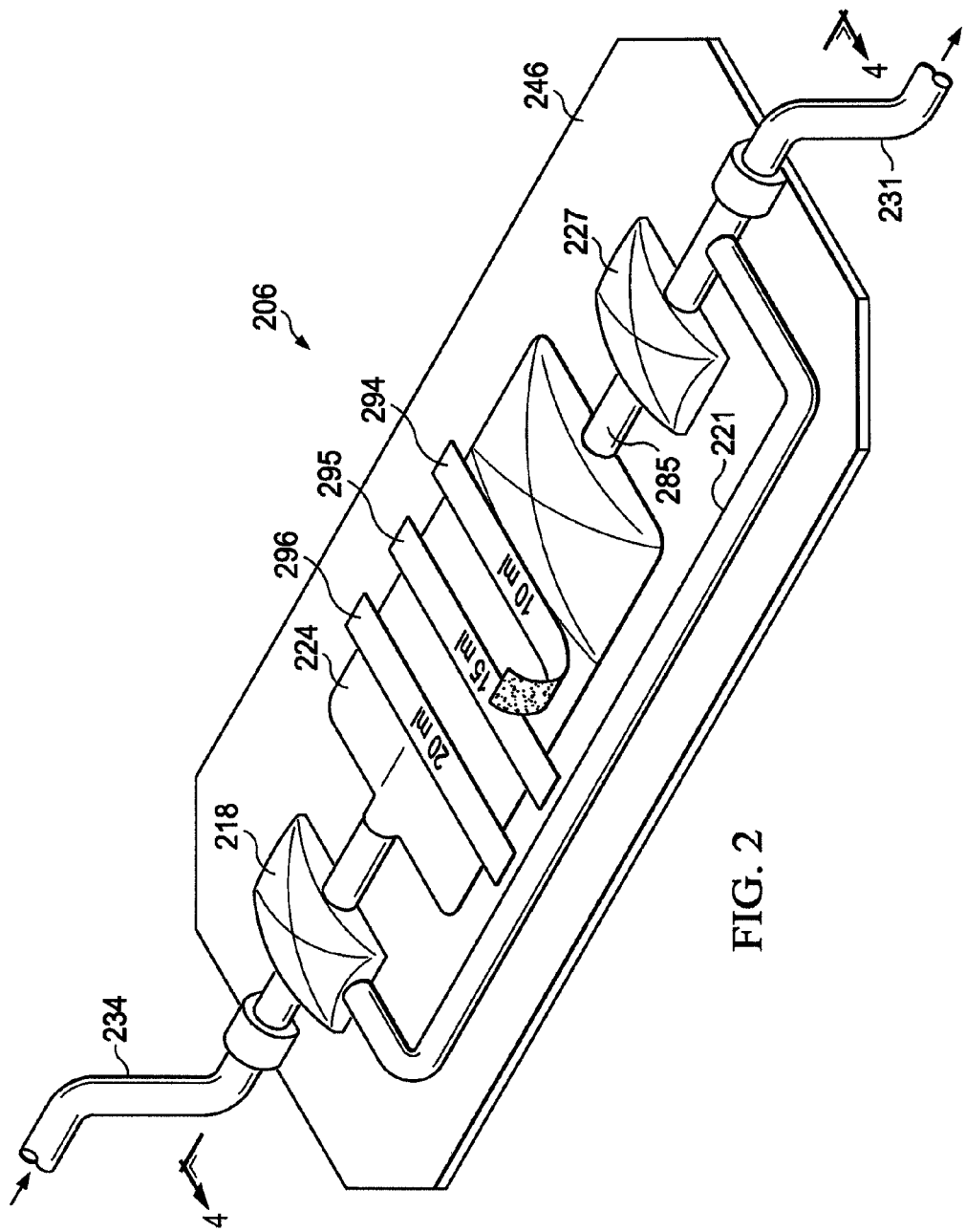
FIG. 2 is a schematic, perspective view of an apparatus for managing liquid flow associated with a tissue site in accordance with an illustrative embodiment.
Figure 6A:
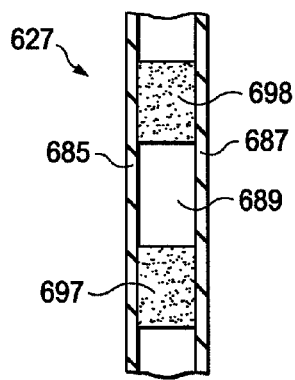
FIG. 6A is a schematic cross-sectional view of a valve in an open position in accordance with an illustrative embodiment.
Figure 6B:
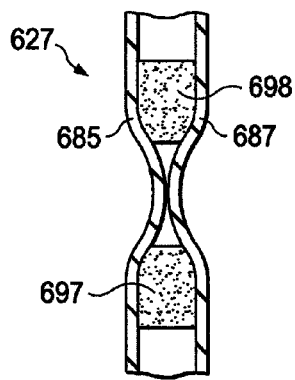
FIG. 6B is a schematic cross-sectional view of a valve in a closed position in accordance with an illustrative embodiment.

Referring now primarily to FIGS. 6A and 6B, a second valve 627, which may be used as the second valve 227 in FIG. 2, is shown according to an illustrative embodiment. In FIG. 6A, the second valve 627 is shown in an open position. In FIG. 6B, the second valve 627 is shown in a closed position. The second valve 627 includes spacers 697 and 698. In an absence of reduced pressure at the second valve 627, the spacers 697 and 698 bias the first wall 685 away from the second wall 687 to form the space 689. The spacers 697 and 698 may be composed of any elastic resilient material that is either formed with apertures or is liquid permeable.

Figure 7:
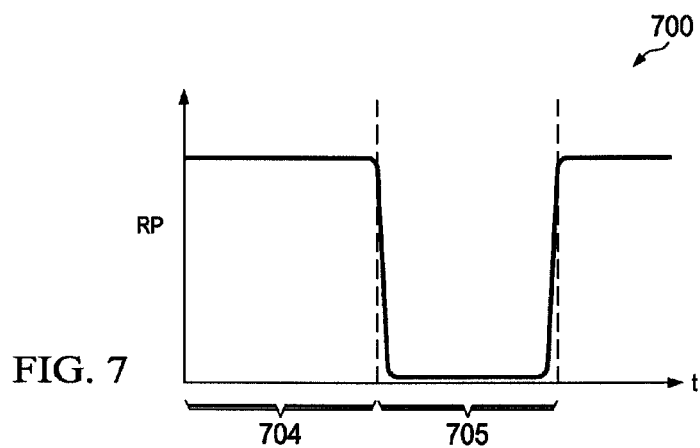
FIG. 7 is a schematic graph illustrating the level of reduced pressure over time in an apparatus for managing liquid flow associated with a tissue site in accordance with an illustrative embodiment.

Referring now primarily to FIG. 7, a schematic graph 700 illustrating the level of reduced pressure over time in an apparatus, such as apparatus 106 in FIG. 1 or apparatus 206 in FIG. 2, for managing liquid flow associated with a tissue site is depicted in accordance with an illustrative embodiment. During time period 704, reduced pressure is applied to the apparatus for managing liquid flow. The reduced pressure may be supplied by a tissue site, which, in turn, receives reduced pressure from a separate reduced-pressure device or source, e.g., the reduced-pressure source 115 in FIG. 1, which may include a controller. Thus, in this example, the separate reduced-pressure device is turned on during time period 704.

During time period 704, the reduced pressure is transferred to a first valve and a second valve, such as a first valve and a second valve described in any of the illustrative embodiments. During time period 704, the first valve is in an open position and the second valve is in a closed position such that a reservoir, as described in any of the illustrative embodiments, fills with a liquid from a liquid source up to a predetermined or maximum volume. The liquid, however, is obstructed from exiting the reservoir and flowing to a tissue site during the time period 704.

During the time period 705, the separate reduced-pressure source that supplies reduced pressure to the tissue site may be turned off, or may supply a relatively lesser amount of reduced pressure than during the time period 704. During the time period 705, the absence of reduced pressure at the first valve and the second valve causes the first valve to have a closed position and the second valve to have an open position. Thus, during the time period 705, the volume of liquid in the reservoir is allowed to exit the reservoir and flow to a tissue site. In one non-limiting example, the reduced pressure may be oscillated between the reduced pressure in the time period 704 and the reduced pressure in the time period 705 so that the flow of liquid to a tissue site may be managed in measured doses. In this example, the reduced pressure supplied by the separate reduced-pressure source to the tissue site may be turned off and on in predetermined time internals, such as the time period 704 and the time period 705.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in a connection to any one embodiment may also be applicable to any other embodiment.

We claim:

1. An apparatus for managing liquid flow associated with a tissue site, the apparatus comprising:
   a first valve in fluid communication with a reduced-pressure source, the first valve movable between an open position and a closed position, wherein the first valve is operable to be activated based on a presence of reduced pressure;
   a second valve in fluid communication with the reduced-pressure source, the second valve movable between an open position and a closed position, wherein the second valve is operable to be activated based on the presence of reduced pressure;
   wherein at least one of the first valve and the second valve is in the closed position to obstruct a flow of a liquid when experiencing reduced pressure;
   a reservoir fluidly coupled to the first valve and the second valve, the reservoir operable to contain a liquid when the second valve is in the closed position; and
   a reduced-pressure conduit in fluid communication with the first valve and the second valve, wherein the reduced-pressure conduit is operable to transmit reduced pressure from the tissue site to the first valve and the second valve.

2. The apparatus of claim 1, wherein the first valve moves from the open position to the closed position in an absence of reduced pressure at the first valve; and wherein the second valve moves from the open position to the closed position in the presence of reduced pressure at the second valve.

3. The apparatus of claim 1, wherein the first valve moves from the closed position to the open position in the presence of reduced pressure at the first valve; wherein the first valve moves from the open position to the closed position in an absence of reduced pressure at the first valve; wherein the second valve moves from the open position to the closed position in the presence of reduced pressure at the second valve; and wherein the second valve moves from the closed position to the open position in an absence of reduced pressure at the second valve.

4. The apparatus of claim 1, wherein the reservoir is disposed between the first valve and the second valve.

5. The apparatus of claim 1, further comprising a set of restriction strips operable to restrict expansion of the reservoir to contain a maximum amount of liquid, wherein the set of restriction strips are disposed over at least a portion of the reservoir.

6. The apparatus of claim 1, further comprising a set of restriction strips operable to restrict expansion of the reservoir to contain a maximum amount of liquid, wherein the set of restriction strips are disposed over at least a portion of the reservoir, and wherein each of the set of restriction strips is removable from the reservoir to increase the maximum amount of the liquid holdable by the reservoir.

7. The apparatus of claim 1, wherein the reduced-pressure conduit is operable to transmit reduced pressure from the tissue site to the first valve and the second valve, and further comprising: a first sheet and a second sheet coupled to the first sheet to at least partially form the reservoir and the reduced-pressure conduit.

8. The apparatus of claim 1, wherein the reduced-pressure conduit is operable to transmit reduced pressure from the tissue site to the first valve and the second valve; further comprising: a first sheet and a second sheet coupled to the first sheet to at least partially form the reservoir and the reduced-pressure conduit; and wherein at least a portion of the first sheet is welded to the second sheet.

9. The apparatus of claim 1, wherein the reduced-pressure conduit is operable to transmit reduced pressure from the tissue site to the first valve and the second valve; further comprising: a first sheet, and a second sheet coupled to the first sheet to at least partially form the reservoir and the reduced-pressure conduit; and wherein the reservoir and the reduced-pressure conduit are at least partially formed by abutting portions of the first sheet and the second sheet.

10. The apparatus of claim 1, wherein the reduced-pressure conduit is operable to transmit reduced pressure from the tissue site to the first valve and the second valve; further comprising: a first sheet, and a second sheet coupled to the first sheet to at least partially form the reservoir and the reduced-pressure conduit; and, further comprising a foam member disposed between the first sheet and the second sheet, wherein the foam member is operable to transfer reduced pressure and the liquid.

11. The apparatus of claim 1, wherein the reduced-pressure conduit is operable to transmit reduced pressure from the tissue site to the first valve and the second valve; further comprising: a first sheet and a second sheet coupled to the first sheet to at least partially form the reservoir and the reduced-pressure conduit; further comprising a foam member disposed between the first sheet and the second sheet, wherein the foam member is operable to transfer reduced pressure and the liquid; and wherein at least a portion of the foam member is included in the reduced-pressure conduit.

12. The apparatus of claim 1, wherein the reduced-pressure conduit is operable to transmit reduced pressure from the tissue site to the first valve and the second valve; further comprising: a first sheet, and a second sheet coupled to the first sheet to at least partially form the reservoir and the reduced-pressure conduit; further comprising a foam member disposed between the first sheet and the second sheet, wherein the foam member is operable to transfer reduced pressure and the liquid; wherein at least a portion of the foam member is included in the reduced-pressure conduit; and wherein a first end of the foam member forms at least a portion of the first valve.

13. The apparatus of claim 1, further comprising a reduced-pressure conduit in fluid communication with at least one of the first valve and the second valve; wherein the reduced-pressure conduit is operable to transmit reduced pressure from the tissue site to the at least one of the first valve and the second valve; further comprising: a first sheet, and a second sheet coupled to the first sheet to at least partially form the reservoir and the reduced-pressure conduit; further comprising a foam member disposed between the first sheet and the second sheet, wherein the foam member is operable to transfer reduced pressure and the liquid; wherein at least a portion of the foam member is included in the reduced-pressure conduit; wherein a first end of the foam member forms at least a portion of the first valve; wherein the first end of the foam member is an enlarged end portion; and wherein the first end of the foam member compresses in the presence of reduced pressure.

14. The apparatus of claim 1, further comprising: a first sheet and a second sheet coupled to the first sheet to at least partially form the reservoir and the reduced-pressure conduit; a foam member disposed between the first sheet and the second sheet, wherein the foam member is operable to transfer reduced pressure and the liquid; and a third sheet coupled to the second sheet to form an inlet conduit, wherein the inlet conduit is operable to transfer the liquid to the reservoir.

15. The apparatus of claim 1, wherein the reduced-pressure conduit is operable to transmit reduced pressure from the tissue site to the at least one of the first valve and the second valve, and further comprising:
   a first sheet;
   a second sheet coupled to the first sheet to at least partially form the reservoir and the reduced-pressure conduit;
   a foam member disposed between the first sheet and the second sheet, wherein the foam member is operable to transfer reduced pressure and the liquid;
   wherein at least a portion of the foam member is included in the reduced-pressure conduit;
   wherein a first end of the foam member forms at least a portion of the first valve;
   wherein the second valve comprises a first wall and a second wall, wherein the first wall is a portion of the first sheet, and wherein the second wall is a portion of the second sheet;
   wherein the first wall and the second wall are operable to draw nearer to one another in the presence of reduced pressure to form the closed position; and
   wherein the first wall and the second wall are operable to move away from one another in an absence of reduced pressure to form the open position.

16. The apparatus of claim 1, wherein the first valve and the second valve are pilot-actuated valves.

17. A method for managing liquid flow associated with a tissue site, the method comprising: providing a valve arrangement having a first valve, a second valve, and a reservoir; receiving reduced pressure at the first valve and the second valve, wherein the first valve and second valve each are moveable between an open position and a closed position; changing a flow status of the first valve in response to receiving reduced pressure at the first valve; receiving a liquid at the reservoir when the first valve is open; changing a flow status of the second valve in response to receiving reduced pressure at the second valve; and obstructing a flow of liquid from the reservoir when the second valve is closed, wherein reduced pressure is received at the first valve and the second valve via a reduced-pressure conduit operable to transmit reduced pressure from the tissue site.

18. The method of claim 17, further comprising:
   closing the first valve in response to an absence of reduced pressure at the first valve;
   obstructing the flow of the liquid from a liquid source to the reservoir in response to closing the first valve;
   opening the second valve in response to the absence of reduced pressure at the second valve; and
   receiving the liquid at the tissue site from the reservoir in response to opening the second valve.

* * * * *